Figures 1, 2:
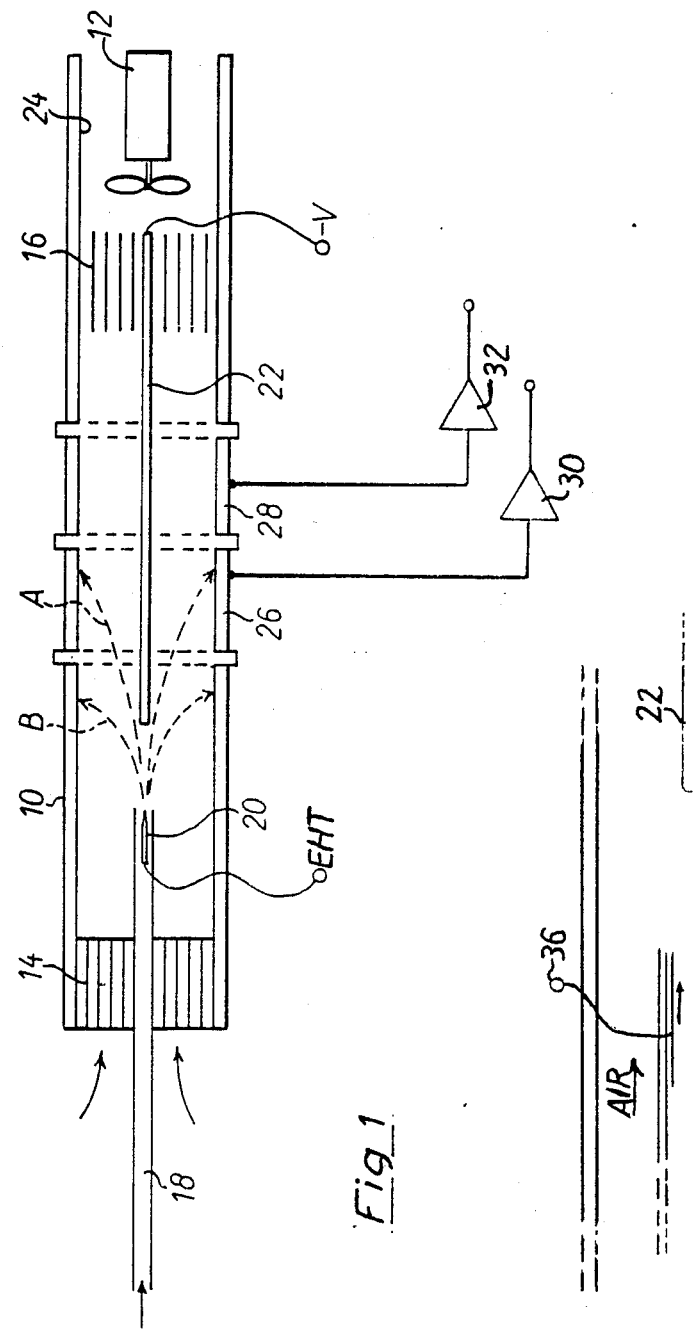

United States Patent [19]

Jenkins

[11] Patent Number: 4,831,254

[45] Date of Patent: May 16, 1989

[54] ION DRIFT DETECTOR

[75] Inventor: Anthony Jenkins, Little Shelford, England

[73] Assignee: Analytical Instruments Limited, Cambridge, United Kingdom

[21] Appl. No.: 7,127

[22] Filed: Jan. 27, 1987

[30] Foreign Application Priority Data

Oct. 25, 1986 [GB] United Kingdom ............... 8625593

[51] Int. Cl.⁴ ............................................. B01D 59/44
[52] U.S. Cl. ..................................... 250/287; 250/286
[58] Field of Search ............... 250/281, 282, 283, 286, 250/287, 288

[56] References Cited

U.S. PATENT DOCUMENTS

| | | | |
|---|---|---|---|
| 3,986,111 | 10/1976 | Sellers | 250/287 |
| 4,023,398 | 5/1977 | French et al. | 250/281 |
| 4,271,357 | 6/1981 | Bradshaw et al. | 250/287 |
| 4,390,784 | 6/1983 | Browning et al. | 250/286 |

Primary Examiner—Bruce C. Anderson
Attorney, Agent, or Firm—Anthony J. Casella; Gerald E. Hespos

[57] ABSTRACT

An ion drift detector comprising an electrically insulating cylindrical tube. A means is provided for establishing along the tube a laminar flow of air into which heavier than air molecules, whose presence is to be detected, can be introduced. An ionizing means is disposed at a location on the central longitudinal axis of the tube for ionizing at least some of the molecules in the laminar flow. Disposed in the tube at a location downstream of the ionizing means there is provided a means for establishing a radial electric field extending across the space between the longitudinal axis and the wall of the tube, such that the ions formed on the axis of the tube are caused to be drifted generally radially across the laminar flow of air under the influence of the radial electric field. The tube also contains an ion collector arrangement which can detect the arrival of ions at different regions along the length of the tube, so that lighter and heavier ions can be distinguished by the extent of longitudinal travel along the cylindrical tube before the ions reach the wall of the tube.

7 Claims, 1 Drawing Sheet

ION DRIFT DETECTOR

DESCRIPTION

The present invention concerns ion drift detectors.

An ion drift detector is already known (see our U.K. Pat. No. 2021787B by which the presence of electron capture constituents in a gas flow can be detected. The known detector comprises an electrically insulating elongate chamber through which the gas flow can be passed and which contains a number of electrodes which are spaced apart in the direction of gas flow. A means, such as a corona discharge, is provided for creating free electrons in the region of one of the electrodes such that at least some of the electrons are captured by the electron capture constituent in the gas flow to form negative ions. An electric field is arranged to be established between said one electrode and a downstream electrode such as to oppose and prevent the travel with the gas flow of free electrons and light negative ions past said downstream electrode while allowing negative ions of heavier mass to be carried by the gas flow past said downstream electrode to a further of the electrodes which acts as a collector. It is these heavier negative ions which are usually of interest and the technique thereby enables the presence of such negative ions to be detected and quantified.

The known ion detector thus relies on displacing the negative ions of interest in an essentially axial path along the chamber to the collector. Whereas this arrangement works satisfactorily in many situations, there is a requirement for greater sensitivity and selectivity which cannot be met by the known device and it is an object of the present invention to provide an ion detector which has improved performance in these respects.

In an ion drift detector in accordance with the present invention, ions are formed in the centre of a cylindrical detector and are caused to be drifted generally radially across a laminar flow of air under the influence of a radical electric field.

Lighter ions are carried rapidly across the radial field, which is maintained inside a metal cylinder, and are only carried a relatively short distance along the cylinder by a flow of air along the cylinder, before striking the cylinder wall. On the other hand, heavier ions travel radially more slowly and are therefore carried further along the cylinder before reaching the cylinder wall. It is the latter, heavier ions which are generally of interest.

The ions thus separated along the cylinder can be collected at different points along the cylinder by suitable ion collectors, where they can be amplified and processed to enable an electrical circuit to provide a signal indicative only of those ions of interest within a narrow band of ionic mass.

In one embodiment it is convenient to establish the radial electric field by the provision of an electrode disposed coaxially within said cylinder, the latter electrode carrying a potential of the polarity the same as the polarity of the charges on the ions.

This detector has the advantages over the known ion detector described initially of greater sensitivity and selectivity.

The invention is described further hereinafter, by way of example only, with reference to the accompanying drawings, wherein:

FIG. 1 is a diagrammatic sectional side view of one embodiment of an ion drift detector in accordance with the present invention; and FIG. 2 is a diagrammatic sectional view (to an larged scale) showing an alternative form of ionization means.

The illustrated detector comprises a long tube 10 along which a laminar flow of (in this case) air is established by the action of a suitable pump or fan 12. It is preferred for respective laminar baffles 14,16 to be positioned at the ends of the tube 10 in order to ensure a laminar flow of air down the tube.

Air which may contain compounds of interest is introduced into the tube 10 by way of a further tube 18 extending through the centre of the upstream laminar baffle 14 and coaxially with the tube 10.

Disposed in the airstream adjacent the outlet of the tube 18 is a point or points 20 connected to a source of e.h.t. for the establishment of a corona discharge by means of which ions are generated in the sampled air stream in the region of said outlet. In alternative arrangements, ions may instead be generated by the action of a radioactive source, a heated filament, a combination of such devices, or any other suitable ionizing means.

Ionic reactions occur in the region of the ion generator 20, certain molecules of interest forming heavy negative ions. Oxygen ions and other hydrated ions are also formed, but such ions are mostly lighter than the ions of interest. All ions are carried away from the region of the point 20 under the influence of the laminar flow of air which is maintained down the tube 10.

Disposed downstream of the region 20, considered in the direction of the laminar air flow, there is arranged to be established an electrical field, at least a component of which is directed radially of the longitudinal axis of the tube 10. In the present embodiment, the radial field is established principally by the provision along the axis of the tube 10 of an elongate electrode 22 connected to a source of negative potential ($-V$). The effect of this negative potential disposed in the path of the negatively charged ions is that such negatively charged ions moving axially towards it are caused to be urged laterally away from the electrode 22 (as illustrated by chain lines in the drawing) so that they eventually hit the inside wall 24 of the tube, heavier ions being displaced less abruptly (see trajectory A) than lighter ones (see trajectory B) and therefore drifting further along the tube 10 before hitting the wall 24. Naturally, in the presently illustrated case where the ionizing means itself involves a high-voltage source, the ionizing voltage on point 20 will also effect to some extent the generation of the radial field. In this case, therefore, the generation of the radial field can be considered to be established by the resultant effect of the electric fields associated with the high voltages on the components 20 and 22.

Thus, ions of different masses strike the wall 24 at different points along the tube 10 where they are collected by one or more tubular ion collectors. In the illustrated embodiment, the ion collectors (two) are shown as annular collecting rings 26 and 28 which are connected to respective conventional amplifying means 30 and 32 for subsequent display and/or electronic analysis, thereby enabling selective detection of molecules of interest in the incoming airstream.

The voltage applied to the coaxial electrode 22 may be adjusted to provide varying field strengths for the radial electric field, thus modifying the trajectories A, B etc. of the various ions and enabling them to be collected at varying points along the tube 10 by suitable manipulation of collector electrode distance and electrode potential.

Whereas the aforegoing description refers to the detection of negative ions, the present invention is equally applicable to the detection of positive ions, should this be required. In the case of positive ion drift, the electrode 22 would of course need to be polarised positively.

In a further alternative arrangement, a multiplicity of collector electrodes can be provided from which a mobility spectrum can be obtained by displaying the collected current from those electrodes in some convenient form, such as by a bar graph display or a recorded output.

FIG. 2 shows an alternative means of ionization using a radioactive source 34 disposed within the tube 18 in place of the electrode 20. The radioactive source is maintained at a potential of a few volts higher than the polarising pin 22 by way of a polarising voltage terminal or connection 36. Thus, for example, for negative ion drift, the radioactive source is maintained at a higher negative potential than the polarising pin 22. The remaining structure of the apparatus is otherwise essentially the same as in the embodiment of FIG. 1.

I claim:

1. An ion drift detector comprising:
   an electrically insulating, elongate, cylindrical tube having a central longitudinal axis;
   means for establishing along the tube a laminar flow of air into which heavier than air molecules, whose presence is to be detected, can be introduced;
   introduction means for introducing air which may contain the heavier than air molecules into said cylindrical tube at a location therealong at which laminar flow exists and at a location generally coaxial with the longitudinal axis of said cylindrical tube;
   means disposed at a location on the central longitudinal axis of the tube for ionizing at least some of the molecules in said laminar flow;
   means disposed in said tube at a location downstream of the ionizing means in the direction of said laminar flow for establishing a radial electric field extending across the space between said longitudinal axis and the wall of the tube, whereby said ions formed on said axis of the cylindrical tube are caused to be drifted generally radially across the laminar flow of air under the influence of the radial electric field; and
   ion collector means on the tube to be able to detect the arrival of ions at different regions along the length of the tube, so that lighter and heavier ions can be distinguished by the extent of longitudinal travel along the cylindrical tube before said ions reach the wall of the tube.

2. An ion drift detector according to claim 1, wherein, for establishing said radial electric field, there is provided on said central longitudinal axis of the cylindrical tube an electrode carrying a potential, the polarity of which is the same as the polarity of the charges on the ions produced by said ionizing means.

3. An ion drift detector according to claim 1, wherein said introduction means comprises a second tube which extends into said cylindrical tube and whose outlet end is disposed coaxially of said cylindrical tube, air containing molecules of possible interest being introduced into said laminar air flow via the second tube.

4. An ion drift detector according to claim 3, wherein the ionizing means comprises a high voltage electrode disposed coaxially within the outlet end of said second tube.

5. An ion drift detector according to claim 1, wherein a laminar flow of air within the cylindrical tube is encouraged by the provision at each end of said tube of a respective plurality of laminar baffles.

6. An ion drift detector according to claim 3, wherein the ionizing means comprises a radioactive source disposed within the outlet end of said second tube.

7. An ion drift detector according to claim 1, wherein said introduction means comprises a second tube which extends into said cylindrical tube and whose outlet end is disposed coaxially of said cylindrical tube, air containing molecules of possible interest being introduced into said laminar air flow via the second tube, and wherein, for establishing said radial electrical field, there is provided on said central longitudinal axis of the cylindrical tube an electrode carrying a potential, the polarity of which is the same as the polarity of the charges on the ions produced by said ionizing means, and wherein the ionizing means comprises a radioactive source disposed within the outlet end of said second tube, the radioactive source being maintained at a potential of the same polarity as, but of greater magnitude than, the potential of said electrode.

* * * * *